(12) United States Patent
Hunt

(10) Patent No.: US 8,034,096 B2
(45) Date of Patent: Oct. 11, 2011

(54) STENT-GRAFT WITH GRAFT TO GRAFT ATTACHMENT

(75) Inventor: James B. Hunt, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 2029 days.

(21) Appl. No.: 10/815,105

(22) Filed: Mar. 31, 2004

(65) Prior Publication Data

US 2005/0222667 A1    Oct. 6, 2005

(51) Int. Cl.
  *A61F 2/06* (2006.01)
(52) U.S. Cl. .................. 623/1.13; 623/1.11
(58) Field of Classification Search .......... 623/1.13, 623/1.1
  See application file for complete search history.

(56) References Cited

U.S. PATENT DOCUMENTS

| | | | |
|---|---|---|---|
| 5,735,892 A | 4/1998 | Myers et al. | 623/1 |
| 5,843,166 A * | 12/1998 | Lentz et al. | 623/1.13 |
| 5,928,279 A | 7/1999 | Shannon et al. | 623/1 |
| 6,001,125 A | 12/1999 | Golds et al. | 623/1 |
| 6,004,348 A | 12/1999 | Banas et al. | 623/1 |
| 6,019,786 A | 2/2000 | Thompson | 623/1 |
| 6,042,605 A | 3/2000 | Martin et al. | 623/1 |
| 6,139,573 A | 10/2000 | Sogard et al. | 623/1.13 |
| 6,270,523 B1 | 8/2001 | Herweck et al. | 623/1.13 |
| 6,309,343 B1 | 10/2001 | Lentz et al. | 600/36 |
| 6,309,413 B1 | 10/2001 | Dereume et al. | 623/1.13 |
| 6,312,462 B1 | 11/2001 | McDermott et al. | |
| 6,346,119 B1 * | 2/2002 | Kuwahara et al. | 623/1.13 |
| 6,383,214 B1 | 5/2002 | Banas et al. | 623/1.14 |
| 6,387,123 B1 * | 5/2002 | Jacobs et al. | 623/1.34 |
| 6,398,803 B1 | 6/2002 | Layne et al. | 623/1.13 |
| 6,579,314 B1 * | 6/2003 | Lombardi et al. | 623/1.44 |
| 6,652,570 B2 | 11/2003 | Smith et al. | 623/1.13 |
| 6,656,215 B1 | 12/2003 | Yanez et al. | 623/1.13 |
| 2001/0034550 A1 * | 10/2001 | Buirge et al. | 623/1.47 |
| 2001/0041928 A1 | 11/2001 | Pavcnik et al. | 623/1.13 |
| 2003/0097174 A1 | 5/2003 | Henderson | 623/1.54 |
| 2003/0171801 A1 | 9/2003 | Bates | 623/1.13 |
| 2003/0181968 A1 | 9/2003 | Xie et al. | 623/1.13 |

FOREIGN PATENT DOCUMENTS

| WO | WO 00/18328 A | 4/2000 |
|---|---|---|
| WO | WO 00/45742 A | 8/2000 |
| WO | WO 2004/022150 A1 | 3/2004 |

OTHER PUBLICATIONS

International Search Report from corresponding PCT Application No. PCT/US2005/009757, dated Sep. 8, 2005, 6 pages.

* cited by examiner

*Primary Examiner* — Corrine M McDermott
*Assistant Examiner* — Melissa Ryckman
(74) *Attorney, Agent, or Firm* — Brinks Hofer Gilson & Lione

(57) ABSTRACT

A stent-graft assembly is provided for a variety of medical treatments. The stent-graft assembly includes a stent disposed between an inner layer of graft material and an outer layer of graft material. The graft layers are effectively secured to the stent by attaching the graft layers together through openings in the structure of the stent. Relative movement between the graft layers and the stent is made possible by providing unattached margins between the attached areas of the graft layers and the edges of the stent openings.

28 Claims, 3 Drawing Sheets

STENT-GRAFT WITH GRAFT TO GRAFT ATTACHMENT

BACKGROUND

The present invention relates generally to medical devices and particularly to a stent assembly with graft layers disposed along luminal and abluminal surfaces of a stent.

Although stent-graft assemblies may be used to treat a number of medical conditions, one common use of stent-graft assemblies relates to the treatment of aneurysms. As those in the art well know, an aneurysm is an abnormal widening or ballooning of a portion of an artery. Generally, this condition is caused by a weakness in the blood vessel wall. High blood pressure and atherosclerotic disease may also contribute to the formation of aneurysms. It is possible for aneurysms to form in blood vessels throughout the vasculature. However, common types of aneurysms include aortic aneurysms, cerebral aneurysms, popliteal artery aneurysms, mesenteric artery aneurysms, and splenic artery aneurysms. If not treated, an aneurysm may eventually rupture, resulting in internal hemorrhaging. In many cases, the internal bleeding is so massive that a patient can die within minutes of an aneurysm rupture. For example, in the case of aortic aneurysms, the survival rate after a rupture can be as low as 20%.

Traditionally, aneurysms have been treated with surgery. For example, in the case of an abdominal aortic aneurysm, the abdomen is opened surgically and the widened section of the aorta is removed. The remaining ends of the aorta are then surgically reconnected. In certain situations the surgeon may choose to replace the excised section of the aorta with a graft material such as Dacron, instead of directly reconnecting the two ends of the blood vessel together. In still other situations, the surgeon may put a clip on the blood vessel at the neck of the aneurysm between the aneurysm and the primary passageway of the vessel. The clip then prevents blood flow from the vessel from entering the aneurysm.

An alternative to traditional surgery is endovascular treatment of the blood vessel with a stent-graft. This alternative involves implanting a stent-graft in the blood vessel across the aneurysm using conventional catheter-based placement techniques. The stent-graft treats the aneurysm by sealing the wall of the blood vessel with a generally impermeable graft material. Thus, the aneurysm is sealed off and the blood flow is kept within the primary passageway of the blood vessel. Increasingly, treatments using stent-grafts are becoming preferred since the procedure results in less trauma and a faster recuperation.

Although stent-grafts are frequently used for treating aneurysms, other medical treatments also use stent-grafts and still other uses are being explored. Additional applications for stent-grafts may also be developed in the future. One example of other uses for stent-grafts is the surgical use of stent-grafts as artificial or replacement vessels. In the case of the vascular system, stent-grafts may be used to replace excised sections of diseased arteries with an artificial replacement vessel. Usually, this would be performed surgically by connecting the ends of the stent-graft to the ends of the artery remaining in the patient's body. Thus, in this application, the stent-graft acts like a blood vessel by directing blood flow through the lumen of the stent-graft and preventing blood flow through the walls of the stent-graft.

Stent-grafts may be used in still other applications as well. For example, stent-grafts may be used to treat stenosed arteries or other vascular conditions. Stent-grafts may also be used to treat a variety of non-vascular organs, such as the esophagus, trachea, colon, biliary tract, urinary tract, prostate and the brain.

One type of stent-graft currently known in the art is constructed with a stent disposed between inner and outer layers of graft material. In order to maintain the integrity of the stent-graft assembly during use, the graft layers must be secured to the stent in some manner. Various techniques for securing graft layers to a stent are currently known. However, the known conventional techniques have numerous problems associated therewith, and an improved manner of securing graft layers to a stent is desired.

One technique for securing graft layers to a stent generally involves adhering the graft layers directly to the stent itself. This is normally accomplished by suturing the graft layers to the struts of the stent or some other part of the stent structure. However, this process must be done manually by specialists using special needles and forceps to sew thread through the graft material, around the struts of the stent, and finally knotting the ends of the thread. This is a very labor intensive task that is time consuming and expensive, thus raising the cost of stent-grafts made by this process.

Moreover, stent-grafts made by suturing the graft layers to the stent lose much of the flexibility inherent in the stent itself. This is generally caused by the direct attachment of the graft layers to the stent structure, which forces the entire assembly (i.e., both the graft layers and the stent) to move simultaneously together. As a result, the graft layers restrict the movement of the stent structure. Flexibility of the assembled stent-graft is important for several reasons. For example, radial flexibility is important to allow the stent-graft to be collapsed onto a delivery system while also allowing the stent-graft to expand at the site of implantation. Axial flexibility is also important to enable the stent-graft to bend as it is guided through tortuous pathways to reach the site of implantation. Even after implantation, axial and radial flexibility remain important when the stent-graft is implanted in an area of the body that is expected to experience frequent movement. However, despite the importance of flexibility, stent-grafts that secure the graft layers directly to the stent are relatively inflexible compared to other types of stents.

Another technique that is used for securing graft layers to a stent generally involves encapsulating the stent or a portion thereof with an inner and an outer layer of graft material. In this type of stent-graft, the two layers of graft material are adhered to each other through open areas in the stent structure. Some additional bounding may also occur between each graft layer and the stent structure itself. Typically, the inner and outer graft layers are adhered by heating the graft layers or with adhesives. However, this type of stent-graft also lacks flexibility as described above. This is due in general to the encapsulated construction of these stent-grafts. In particular, the areas in which the two graft layers are attached abut against the structure of the stent, thereby forcing the graft layers to move together with the stent. This causes the graft layers to restrict the movement of the stent structure. Thus, even when the graft layers are not directly secured to the stent as described, the graft layers are still unable to move independently of the stent.

Accordingly, it is apparent to the inventor that a stent-graft is desired with improved flexibility which allows the graft layers of a stent-graft to move relative to the stent. A solution to these and other problems is described more fully below.

BRIEF SUMMARY

A stent-graft assembly is provided with an inner layer of graft material and an outer layer of graft material secured to a stent. The graft layers are secured to each other through openings in the stent structure. Unattached margin areas are further provided between the attached areas of the graft layers and the edges of the openings. One of the advantages of the stent-graft is that it is easier and less costly to make. Another advantage is that the stent-graft is more flexible than conventional stent-grafts. Additional details and advantages are provided below.

BRIEF DESCRIPTION OF SEVERAL VIEWS OF THE DRAWINGS

The invention may be more fully understood by reading the following description in conjunction with the drawings, in which.

DETAILED DESCRIPTION

Figure 1:
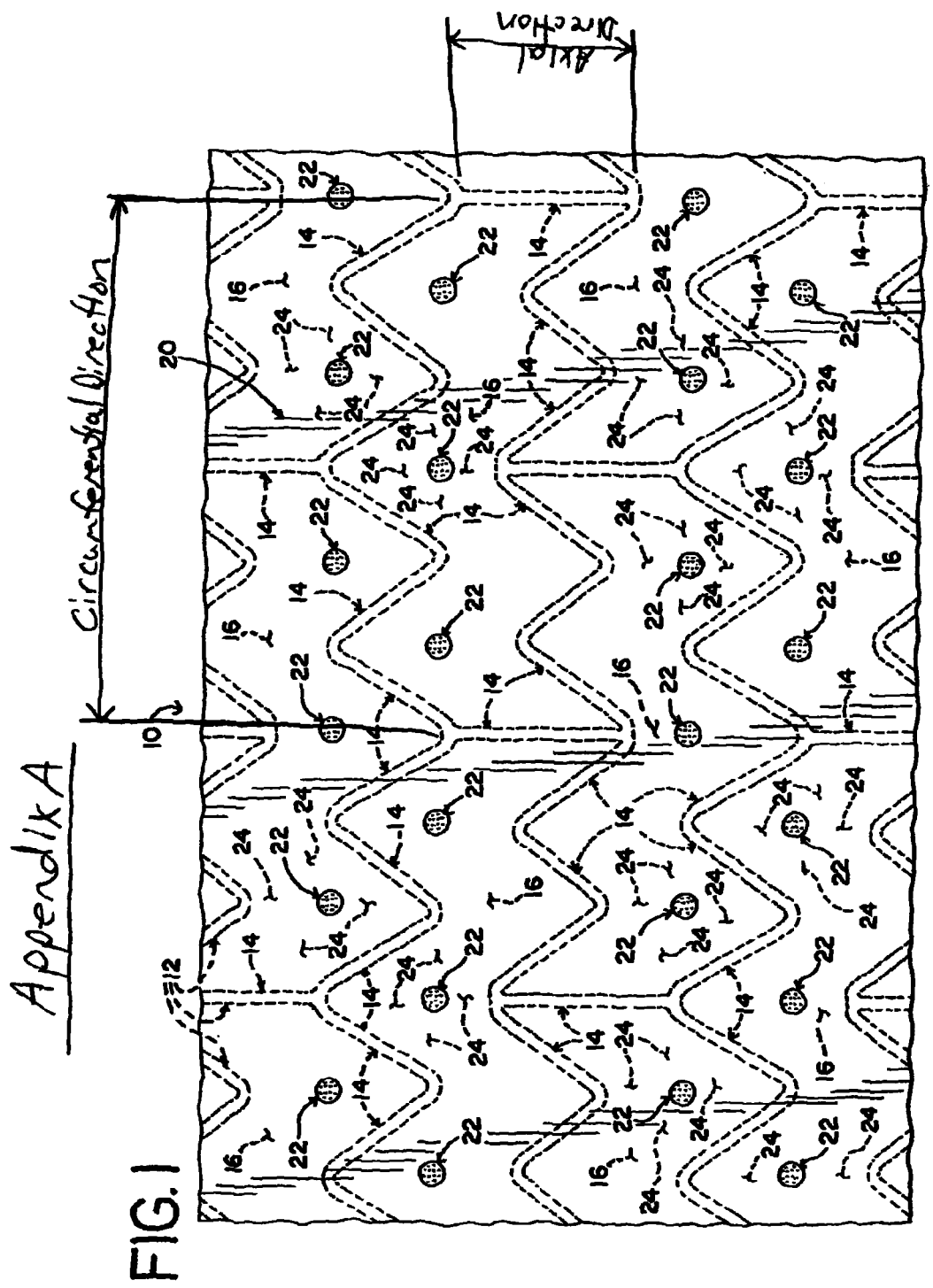
FIG. 1 is a top plan view of a portion of one embodiment of a stent-graft assembly.
Figure 2:
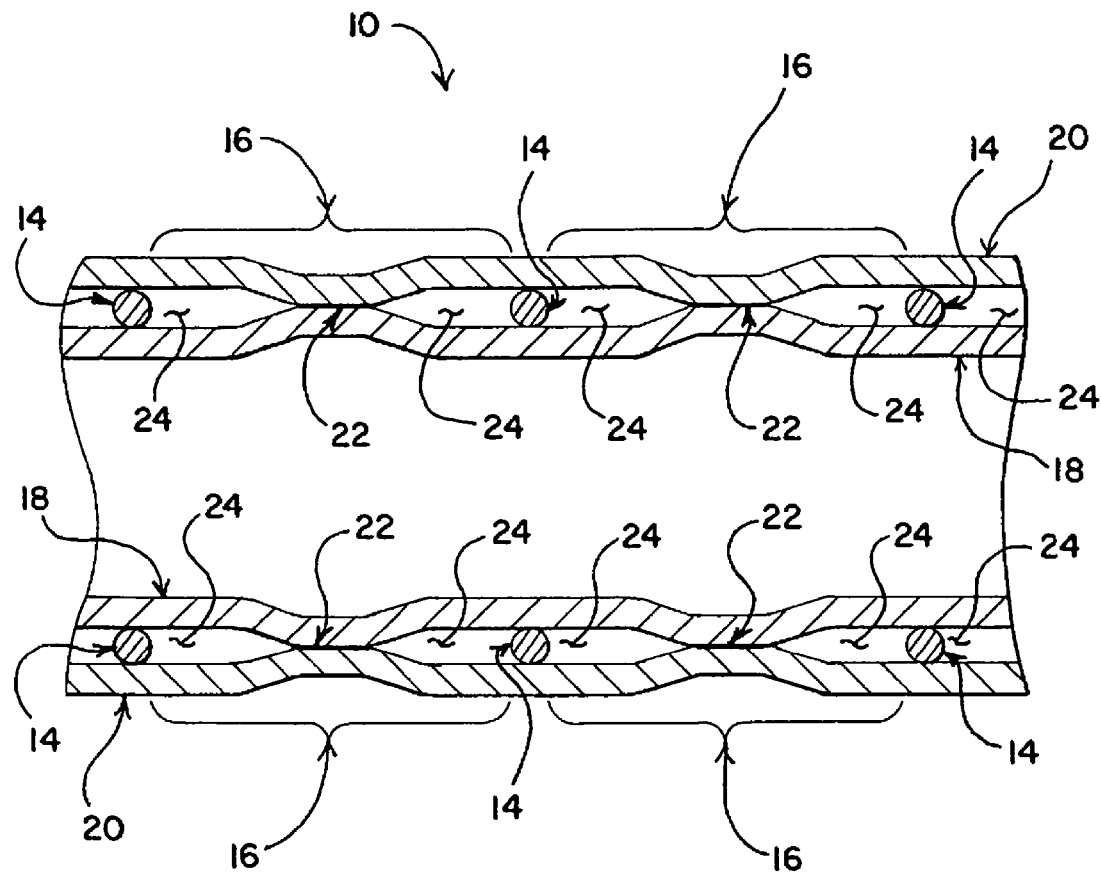
FIG. 2 is a cross sectional view of the stent-graft assembly.

Referring now to the drawings, a stent-graft assembly 10 is shown. The stent-graft 10 includes a stent 12 with an inner layer 18 of graft material disposed along the luminal surface of the stent 12 and an outer layer 20 of graft material disposed along the abluminal surfaces of the stent 12. As shown in the figures, it is preferable for the graft layers 18, 20 to cover the entire luminal and abluminal surfaces. However, it is also possible for the graft layers 18, 20 to cover only a portion of the stent 12.

Various types of stents 12 may be used with the invention. For example, stents may be made from numerous metals and alloys, including stainless steel, nitinol, cobalt-chrome alloys, amorphous metals, tantalum, platinum, gold and titanium. Stents may also be made from non-metallic materials, such as thermoplastics and other polymers. The structure of the stent may also be formed in a variety of ways to provide a suitable intraluminal support structure. For example, stents may be made from a woven wire structure, a laser-cut cannula, individual interconnected rings, or any other type of stent structure that is known in the art. Regardless of the particular construction of the stent, it is usually desirable for the stent to be flexible in several directions, including both radial and axial flexibility. Stents may also be designed to be either balloon-expandable or self-expandable, depending on the particular application of the stent.

In general, most stents are formed of a support structure having a plurality of radial openings that extend through the structure between the luminal surface of the stent and the abluminal surface of the stent. As shown in the figures, the support structure of the stent 12 may be a pattern of interconnected struts 14. The edges of the struts 14 define a series of open areas 16 that extend radially through the support structure. The arrangement, shape and size of the open areas 16 may vary depending on the geometry of the support structure that is used, and the open areas 16 which are shown are only one example of the many possibilities.

Many different types of graft materials may also be used for the inner and outer graft layers 18, 20. Common examples of graft materials currently used include expandable polytetrafluoroethylene (ePTFE), polytetrafluoroethylene (PTFE), Dacron, polyester, fabrics and collagen. However, graft materials may be made from numerous other materials as well, including both synthetic polymers and natural tissues. One graft material that holds particular promise in certain applications is small intestine submucosa (SIS). As those in the art know, SIS material includes growth factors that encourage cell migration within the graft material, which eventually results in the migrated cells replacing the graft material with organized tissues. The graft layers 18, 20 may be formed using a variety of techniques already known to the art. For example, sheets of graft material may be rolled into tubes with the side edges secured together. Unitary tubes may also be formed using a mandrel or the like, which are then coaxially inserted into or drawn over the stent 12. The graft layers 18, 20 may also be formed directly within and on the stent 12. In certain applications, it may also be helpful to impregnate or coat the graft layers 18, 20 with various therapeutic drugs that are well-known to those in the art.

As shown in the figures, the inner graft layer 18 and the outer graft layer 20 are secured together through the open areas 16. Several methods of securing together the graft layers 18, 20 are possible, depending on the particular needs of the application. For example, sutures made from polypropylene thread or other types of thread may be used to sew the inner and outer layers 18, 20 together. The use of sutures for securing graft material to a stent is generally known, but so far this technique has been limited to securing graft materials directly to a stent. One disadvantage that is sometimes experienced with current suturing techniques is the formation of endoleaks through the needle holes that are created in the graft material. Other examples of methods for securing together the inner and outer graft layers 18, 20 include thermal bonding, such as welding or sintering, and the use of adhesives.

As shown, the area of attachment 22 between the inner and outer layers 18, 20 is smaller than the entire open area 16 through which the layers 18, 20 are attached. Thus, only a portion of the inner and outer graft layers 18, 20 are attached through the open areas 16. In particular, unattached margins 24 are formed between each of the attached areas 22 and the edges of the open areas 16 (i.e., the edges of the struts 14). Unlike the areas of attachment 22 where the inner and outer layers 18, 20 are secured together, the unattached margins 24 are areas where the inner and outer layers 18, 20 are not secured together. The unattached margins 24 may be located either axially or circumferentially between the attached areas 22 and the struts 14.

The unattached margins 24 are particularly important because the unattached margins 24 allow the inner and outer graft layers 18, 20 to move relative to the stent 12. For example, where the unattached margins 24 are arranged along the same direction as shown, the struts 14 of the stent 12 can move between the graft layers 18, 20 through the unattached margins 14. This results in a stent-graft assembly 10 that is more flexible than current stent-grafts which either secure the graft layers to the stent struts or encapsulate the stent in graft material. In order to increase the flexibility of the stent-graft 10, it is preferred that the unattached margins 24 are located peripherally all around each of attached areas 22, including both axially and circumferentially between the attached areas 22 and the struts 14. Thus, with the stent-graft assembly 10 that is shown, the graft layers 18, 20 may move forward and rearward, side-to-side, and any other direction relative to the stent 12. To further increase the relative movement that is possible, it is preferred that the site of the attached areas 22 is less than the size of the unattached margins 24.

Figure 3:
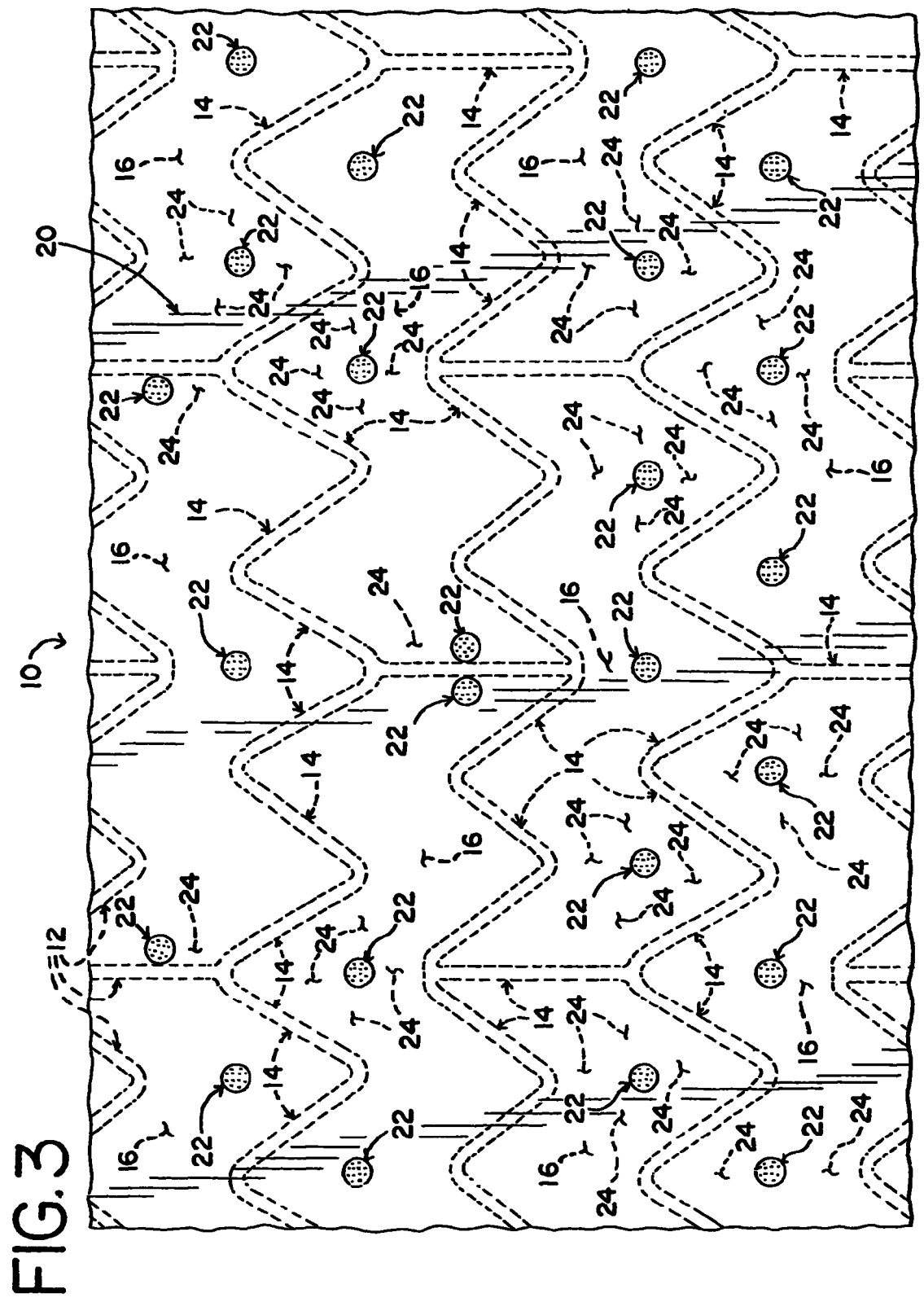
FIG. 3 is a top plan view of a portion of another embodiment of a stent-graft assembly.

Other configurations of the attached areas and the unattached areas are also possible. For example, if flexibility is desired in one direction but not in another direction, the attached areas 22 may be positioned to restrict relative movement in one direction between the graft layers 18, 20 and the stent 12 while allowing movement in another direction. One such configuration may involve positioning at least some of the attached areas 22 adjacent struts 14 extending in one direction while providing unattached margins 24 between the attached areas 22 and struts 14 extending in another direction. For example, as shown in FIG. 3, if attached areas 22 are positioned adjacent opposite sides of a longitudinally extending strut 14, relative movement between the graft layers 18, 20 and the stent 12 will be restricted in the circumferential direction. However, if unattached margins 24 are provided between the attached areas 22 and circumferentially extending struts 14, relative movement will be possible in the axial direction.

The advantages of the invention are now apparent. Compared to traditional stent-grafts where the graft material is secured directly to the stent struts, the stent-graft 10 which has been described may be easier and less expensive to make. The reason for this is that the graft layers 18, 20 are secured together through the open areas 16 in the stent structure instead of being secured to the structure of the stent. This avoids the difficulty of threading sutures around the stent struts. Moreover, it is possible that positioning of the attached areas 22 between the graft layers 18, 20 may be less crucial compared to when the graft layers are secured directly to stent struts. Thus, even when conventional sutures are used to secure the two graft layers 18, 20 together, the labor required may be less than traditional suturing techniques. Moreover, the labor required to secure the graft layers 18, 20 may be reduced even further if thermal bonding is used to secure together the graft layers 18, 20. For example, in this alternative, the two graft layers 18, 20 may be secured together simply by welding the layers 18, 20 together through the open areas 16 without the need for sutures.

The stent-graft assembly 10 is also more flexible than stent-graft assemblies with graft layers secured directly to the stent structure or stent-graft assemblies with graft material encapsulated onto the stent structure. Previous methods of securing graft materials to a stent structure restrict the movement of the graft material relative to the stent. Thus, conventional stent-graft assemblies are considerably less flexible than the underlying stents themselves. The invented stent-graft 10 solves this problem by providing unattached margins 24 between the attached areas 22 of the graft layers 18, 20 and the edges of the open areas 16. This allows the graft layers 18, 20 and the stent 12 to move relative to each other during flexure by permitting the stent structure to move through the unattached margins 24. The maximum amount of flexibility is possible when unattached margins 24 are provided all around the attached areas 22. For example, when unattached margins 24 are provided in at least longitudinal and circumferential directions, the finished stent-graft assembly 10 may be freely flexed in various ways, including angular bending, radial expansion-compression, and even twisting. Other configurations are also possible, however. The effectiveness and simplicity of this approach to the problem of flexibility in stent-grafts makes this solution especially desirable.

The invented stent-graft 10 may also be particularly useful in certain applications, although the concepts taught herein have broad applicability. For example, the stent-graft 10 may be constructed with graft layers 18, 20 made from SIS material. Although the SIS graft layers 18, 20 may be secured together with sutures, thermal bonding may also be used to avoid the introduction of foreign materials into the stent-graft 10. This may produce a stent-graft that is well-suited for replacement vessel applications, since the SIS material tends to become remodeled into the surrounding tissues after implantation.

Accordingly, it is now apparent that there are many advantages of the invention provided herein. In addition to the advantages that have been described, it is also possible that there are still other advantages that are not currently recognized but which may become apparent at a later time.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein.

I claim:

1. A stent-graft assembly, comprising:
   at least one unitary stent structure comprising a luminal surface and an abluminal surface and having at least a first radial opening and a second radial opening, said first and second radial openings being axially and circumferentially defined by a plurality of struts, said first and second radial openings extending through said stent structure between said luminal surface and said abluminal surface, wherein said first and second radial openings are spaced apart along a first direction;
   a first graft layer disposed along at least a portion of said luminal surface of said stent structure thereby fully covering luminal sides of said first and second radial openings;
   a second graft layer disposed along at least a portion of said abluminal surface of said stent structure thereby fully covering abluminal sides of said first and second radial openings;
   a first attached area securing said first graft layer and said second graft layer together through a portion of said first radial opening, wherein a first unattached margin in which said first and second graft layers are not secured to each other is disposed between said first attached area and an edge of said first radial opening;
   a second attached area securing said first graft layer and said second graft layer together through a portion of said second radial opening, wherein a second unattached margin in which said first and second graft layers are not secured to each other is disposed between said second attached area and an edge of said second radial opening; and
   wherein said first and second unattached margins are oriented along said first direction and on a same side of said first and second attached areas, thereby allowing said first and second graft layers to move along said first direction relative to said stent.

2. The stent-graft assembly according to claim 1, wherein a size of said first attached area is less than a size of said first unattached margin and a size of said second attached area is less than a size of said second unattached margin.

3. The stent-graft assembly according to claim 1, wherein said first direction is axial.

4. The stent-graft assembly according to claim 1, wherein said first direction is circumferential.

5. The stent-graft assembly according to claim 1, wherein said first attached area is positioned adjacent another edge of said first radial opening and said second attached area is positioned adjacent another edge of said second radial opening, said first and second attached areas thereby being disposed on opposite sides of said struts, whereby said first and second graft layers are restricted from moving along a second direction relative to said stent.

6. The stent-graft assembly according to claim 5, wherein said first direction is axial and said second direction is circumferential.

7. The stent-graft assembly according to claim 1, wherein said first unattached margin extends peripherally all around said first attached area and said second unattached margin extends peripherally all around said second attached area.

8. The stent-graft assembly according to claim 7, wherein a size of said first attached area is less than a size of said first unattached margin and a size of said second attached area is less than a size of said second unattached margin.

9. The stent-graft assembly according to claim 1, wherein:
   a third unattached margin whereby said first and second graft layers are not secured to each other is disposed between said first attached area and an edge of said first radial opening;
   a fourth unattached margin whereby said first and second graft layers are not secured to each other is disposed between said second attached area and an edge of said second radial opening; and
   said third and fourth unattached margins are oriented along a second direction, thereby allowing said first and second graft layers to move along said second direction relative to said stent, said second direction being different than said first direction.

10. The stent-graft assembly according to claim 9, wherein a size of said first attached area is less than a size of said third unattached margin and a size of said second attached area is less than a size of said fourth unattached margin.

11. The stent-graft assembly according to claim 1, wherein said first graft layer covers substantially all of said luminal surface of said stent structure and said second graft layer covers substantially all of said abluminal surface of said stent structure.

12. The stent-graft assembly according to claim 1, wherein said first and second attached areas are attached using sutures.

13. The stent-graft assembly according to claim 1, wherein said first and second attached areas are attached by thermal bonding.

14. The stent-graft assembly according to claim 1, wherein said first and second graft layers comprise a synthetic polymer.

15. The stent-graft assembly according to claim 1, wherein first and second graft layers comprise small intestine submucosa.

16. The stent-graft assembly according to claim 1, wherein said first and second attached areas are attached by thermal bonding; and said first and second graft layers comprise a synthetic polymer.

17. The stent-graft assembly according to claim 16, wherein:
   a third unattached margin whereby said first and second graft layers are not secured to each other is disposed between said first attached area and an edge of said first radial opening;
   a fourth unattached margin whereby said first and second graft layers are not secured to each other is disposed between said second attached area and an edge of said second radial opening; and
   said third and fourth unattached margins are oriented along a second direction, thereby allowing said first and second graft layers to move along said second direction relative to said stent, said second direction being different than said first direction.

18. The stent-graft assembly according to claim 17, wherein a size of said first attached area is less than a size of said first unattached margin and a size of said third unattached margin and a size of said second attached area is less than a size of said second unattached margin and a size of said fourth unattached margin.

19. The stent-graft assembly according to claim 18, wherein said first graft layer covers substantially all of said luminal surface of said stent structure and said second graft layer covers substantially all of said abluminal surface of said stent structure.

20. The stent-graft assembly according to claim 17, wherein first and second graft layers comprise small intestine submucosa; and said first and second attached areas are attached using sutures.

21. The stent-graft assembly according to claim 20, wherein:
   a third unattached margin whereby said first and second graft layers are not secured to each other is disposed between said first attached area and an edge of said first radial opening;
   a fourth unattached margin whereby said first and second graft layers are not secured to each other is disposed between said second attached area and an edge of said second radial opening; and
   said third and fourth unattached margins are oriented along a second direction, thereby allowing said first and second graft layers to move along said second direction relative to said stent, said second direction being different than said first direction.

22. The stent-graft assembly according to claim 21, wherein a size of said first attached area is less than a size of said first unattached margin and a size of said third unattached margin and a size of said second attached area is less than a size of said second unattached margin and a size of said fourth unattached margin.

23. The stent-graft assembly according to claim 22, wherein said first graft layer covers substantially all of said luminal surface of said stent structure and said second graft layer covers substantially all of said abluminal surface of said stent structure.

24. The stent-graft assembly according to claim 17, wherein first and second graft layers comprise small intestine submucosa; and said first and second attached areas are attached by thermal bonding.

25. The stent-graft assembly according to claim 24, wherein:
   a third unattached margin whereby said first and second graft layers are not secured to each other is disposed between said first attached area and an edge of said first radial opening;
   a fourth unattached margin whereby said first and second graft layers are not secured to each other is disposed between said second attached area and an edge of said second radial opening; and
   said third and fourth unattached margins are oriented along a second direction, thereby allowing said first and second graft layers to move along said second direction relative to said stent, said second direction being different than said first direction.

26. The stent-graft assembly according to claim 25, wherein a size of said first attached area is less than a size of said first unattached margin and a size of said third unattached margin and a size of said second attached area is less than a size of said second unattached margin and a size of said fourth unattached margin.

27. The stent-graft assembly according to claim 26, wherein said first graft layer covers substantially all of said luminal surface of said stent structure and said second graft layer covers substantially all of abluminal surface of said stent structure.

28. A stent-graft assembly, comprising:
- a stent structure comprising a luminal surface and an abluminal surface and having at least a first radial opening and a second radial opening, said first and second radial openings extending through said stent structure between said luminal surface and said abluminal surface, wherein said first and second radial openings are spaced apart along a first direction;
- a first graft layer disposed along at least a portion of said luminal surface of said stent structure thereby fully covering luminal sides of said first and second radial openings;
- a second graft layer disposed along at least a portion of said abluminal surface of said stent structure thereby fully covering abluminal sides of said first and second radial openings;
- a first attached area securing said first graft layer and said second graft layer together through a portion of said first radial opening, wherein a first unattached margin in which said first and second graft layers are not secured to each other is disposed between said first attached area and an edge of said first radial opening;
- a second attached area securing said first graft layer and said second graft layer together through a portion of said second radial opening, wherein a second unattached margin in which said first and second graft layers are not secured to each other is disposed between said second attached area and an edge of said second radial opening;
- wherein said first and second unattached margins are oriented along said first direction and on a same side of said first and second attached areas, thereby allowing said first and second graft layers to move along said first direction relative to said stent; and
- wherein said first unattached margin extends peripherally all around said first attached area and said second unattached margin extends peripherally all around said second attached area.

* * * * *